US006979820B2

(12) United States Patent
Ke et al.

(10) Patent No.: US 6,979,820 B2
(45) Date of Patent: Dec. 27, 2005

(54) CD SEM AUTOMATIC FOCUS METHODOLOGY AND APPARATUS FOR CONSTANT ELECTRON BEAM DOSAGE CONTROL

(75) Inventors: Chih-Ming Ke, Hsin-Chu (TW); Chien-Hsun Lin, Hsin-Chu (TW); Yao-Ching Ku, Hsin-Chu (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 59 days.

(21) Appl. No.: 10/628,914

(22) Filed: Jul. 29, 2003

(65) Prior Publication Data

US 2005/0023463 A1 Feb. 3, 2005

(51) Int. Cl.$^7$ ............................................. G01N 23/225
(52) U.S. Cl. ....................... 250/307; 250/310; 250/397; 345/771
(58) Field of Search ................................ 250/307, 310, 250/397; 345/771

(56) References Cited

U.S. PATENT DOCUMENTS

| 5,025,165 | A | | 6/1991 | Chen et al. ............... 250/491.1 |
| 5,916,716 | A | | 6/1999 | Butsch et al. .................. 430/30 |
| 6,066,849 | A | | 5/2000 | Masnaghetti et al. ....... 250/310 |
| 6,084,238 | A | * | 7/2000 | Todokoro et al. ........... 250/310 |
| 6,114,681 | A | | 9/2000 | Komatsu ................. 250/201.3 |
| 6,130,432 | A | | 10/2000 | Pfeiffer et al. ....... 250/396 ML |
| 2003/0218133 | A1 | * | 11/2003 | Petrov et al. ............... 250/310 |
| 2004/0211899 | A1 | * | 10/2004 | Ezumi et al. ............... 250/310 |

OTHER PUBLICATIONS

"193nm Resist Shrinkage", by Su et al., Solid State Technology, May 2001, pp. 52–54 and 57.
U.S. Appl. No. 10/047,266, Filed Jan. 14, 2002, "Reducing Photoresist Shrinkage via Plasma Treatment", assigned to the Same Assignee.

* cited by examiner

Primary Examiner—Nikita Wells
Assistant Examiner—Zia R. Hashmi
(74) Attorney, Agent, or Firm—Thomas, Kayden, Horstemeyer & Risley

(57) ABSTRACT

A method and apparatus for scanning electron microscope measurements which maintains a constant e-beam dose to the surface of a wafer being measured and thereby maintains a constant resist shrinkage. The apparatus provides a magnetic lens, a movable wafer holder to adjust the distance between a wafer and the magnetic lens, an image detector, means to determine the distance between the wafer and the magnetic lens, a retarding voltage applied to the wafer holder, means to adjust the retarding voltage, and means to focus the magnetic lens. The apparatus also provides feedback systems between the movable wafer holder and the means to determine the distance between the wafer and the magnetic lens, between the image detector and the means to adjust the retarding voltage, and between the image detector and means to focus the magnetic lens so these adjustments can be made automatically. The method first sets the distance between the wafer and the magnetic lens. The method next determines the charge on the wafer and adjusts the retarding voltage accordingly, thereby maintaining a constant accelerating voltage for the electron beam regardless of charge on the wafer. Finally the method focuses the magnetic objective lens. Maintaining a constant accelerating voltage for the electron beam regardless of charge on the wafer maintains constant resist shrinkage regardless the amount of charge on the wafer.

30 Claims, 2 Drawing Sheets

CD SEM AUTOMATIC FOCUS METHODOLOGY AND APPARATUS FOR CONSTANT ELECTRON BEAM DOSAGE CONTROL

BACKGROUND OF THE INVENTION (1) Field of the Invention

This invention relates to a method and apparatus for measuring critical dimensions in resist for 193 nanometer or 157 nanometer lithography which maintains constant resist shrinkage.

(2) Description of the Related Art

A paper entitled "193 nm resist shrinkage", by Su et al., Solid State Technology, May 2001, pages 52–54 and 57, describes problems encountered in 193 nanometer lithography due to variable shrinkage of the resist caused by exposure to an electron beam during critical dimension measurement of the resist.

U.S. Pat. No. 6,114,681 to Komatsu describes an automatic focus control system for an electron beam column.

U.S. Pat. No. 5,916,716 to Butsch et al. describes a method for compensating for repeating pattern deviations such as across chip line width variations in e-beam lithography.

U.S. Pat. No. 6,130,432 to Pfeiffer et al. describes a particle beam exposure system with dynamic focusing.

U.S. Pat. No. 5,025,165 to Chen et al. describes a method of using an e-beam lithography system that comprises optical alignment of a semiconductor body to overcome charging problems.

U.S. Pat. No. 6,066,849 to Masnaghetti et al. describes a method and apparatus for generating an image of a specimen with a scanning electron microscope.

A patent application Ser. No. 10/047,266; filed Jan. 14, 2003; entitled "Reducing Photoresist Shrinkage via Plasma Treatment"; and assigned to the same assignee describes using plasma treatment to reduce photoresist shrinkage. The plasma treatment is carried out prior to critical dimension measurement using an electron beam and decreases shrinkage of the photoresist due to the measurement.

SUMMARY OF THE INVENTION

Critical dimension, CD, control is increasingly important in 193 nm, 157 nm, and especially for sub-130 nm lithography. Scanning electron microscope, SEM, CD monitoring is necessary to achieve adequate CD control. However, SEM e-beam dosage can have a strong effect on shrinkage of resists used for 193 nm, 157 nm, and sub-130 nm lithography. Automatic CD SEM measurement using a low or constant e-beam dose helps to maintain CD control. However, charge on the wafer surface will result in a variable e-beam dosage across the wafer resulting in variable resist shrinkage making CD control difficult or impossible. This charge on the wafer surface is the result of and is dependent on preceding process steps seen by the wafer and will be different for 193 nm, 157 nm, or sub-137 nm lithography.

CD control is one of the major challenges for sub-130 nm lithography. Feed forward systems can be used to establish a CD bias but variable shrinkage caused by variability of e-beam dosage in SEM measurement causes significant problems in implementing a feed forward system.

It is a principle objective of this invention to provide a method of monitoring critical dimensions on a wafer using a scanning electron microscope while maintaining a constant e-beam dosage across the wafer.

It is another principle objective of this invention to provide apparatus for monitoring critical dimensions on a wafer using a scanning electron microscope while maintaining a constant e-beam dosage across the wafer.

These objectives are achieved with a method and apparatus for scanning electron microscope measurements that first focuses to account for wafer thickness variation, next determines the retarding potential applied to the wafer holder thereby determining the wafer surface voltage, and finally focuses the magnetic objective lens.

The apparatus comprises an electron beam source, an image detector, a magnetic objective lens, a wafer holder, means for positioning the wafer holder, means for determining the distance between the magnetic objective lens and the top surface of a wafer placed on the wafer holder, means to supply a retarding voltage between the wafer holder and ground potential, and means to supply a focusing current to the magnetic objective lens. The apparatus also comprises feedback systems to automatically position the wafer holder, automatically determine the focusing current for the magnetic objective lens, and automatically determine the retarding voltage.

In the method of this invention a wafer is placed on the wafer holder. The first step of the method of this invention is to position the wafer holder to provide a specific distance between the magnetic objective lens and the top surface of the wafer. There is feedback between the means for determining the distance between the magnetic objective lens and the top surface of the wafer and the means to position the wafer holder so that this specific distance can be provided automatically.

The next step of the method of this invention is to use a retarding voltage applied to the backside of the wafer and to focus the image on the wafer by adjusting the wafer backside voltage. During wafer processing charge accumulates on the wafer, often referred to as wafer charge, causing a voltage on the wafer surface. Since the charge on the wafer is electronic charge the wafer has a negative voltage. This negative voltage on the wafer will repel the electron beam of the SEM, scanning electron microscope. The retarding voltage is the voltage applied to the specimen, in this example a wafer, to compensate for the wafer voltage caused by the charge buildup on the wafer. The voltage of the wafer surface or so-called "wafer charge" determines the amount of adjustment the retarding voltage must provide. The wafer charge tends to repel incident electrons in the electron beam. In some cases the scanning electron microscope image cannot be focused because most of the electrons having low acceleration voltage are repelled by the wafer charge. The retarding voltage is used to compensate for the voltage caused by the wafer charge. The retarding voltage is automatically adjusted to focus the electron beam on the wafer surface for a particular wafer height. Using a retarding voltage automatically focuses the electron beam keeps the wafer surface landing voltage a constant by compensating for the voltage on the wafer caused by the wafer charge. This insures the wafer surface of each wafer see an electron beam having electrons with the same amount of energy. This step is especially important for low accelerating voltage applications, such as about 300 volts, and/or on highly charged wafers, such as wafers having a negative voltage with a magnitude of greater than 100 volts. After automatically adjusting the wafer backside voltage, the wafer surface will have the same effective landing voltage to generate sufficient secondary electrons to form the scanning electron microscope image. An automatic image detection function used to provide feedback for automatically adjusting the retarding voltage is the key to providing a constant landing voltage. Since all the wafers see an SEM electron beam having the same energy, the resist shrinkage will be the same for wafers having resist for 193 nm, ArF, or for 157 nm, $F_2$.

The next step of the invention is to adjust the current to the magnetic objective lens of focus the magnetic objective lens.

These steps must be performed in the specific sequence of first focusing to account for wafer thickness variation, next determination of the retarding potential applied to the wafer holder in order to compensate for charge on the wafer, and finally focusing the magnetic objective lens. Following these steps in this sequence will maintain a constant e-beam dose during SEM measurements and will avoid variable resist shrinkage.

DESCRIPTION OF THE PREFERRED EMBODIMENTS

Figure 1:
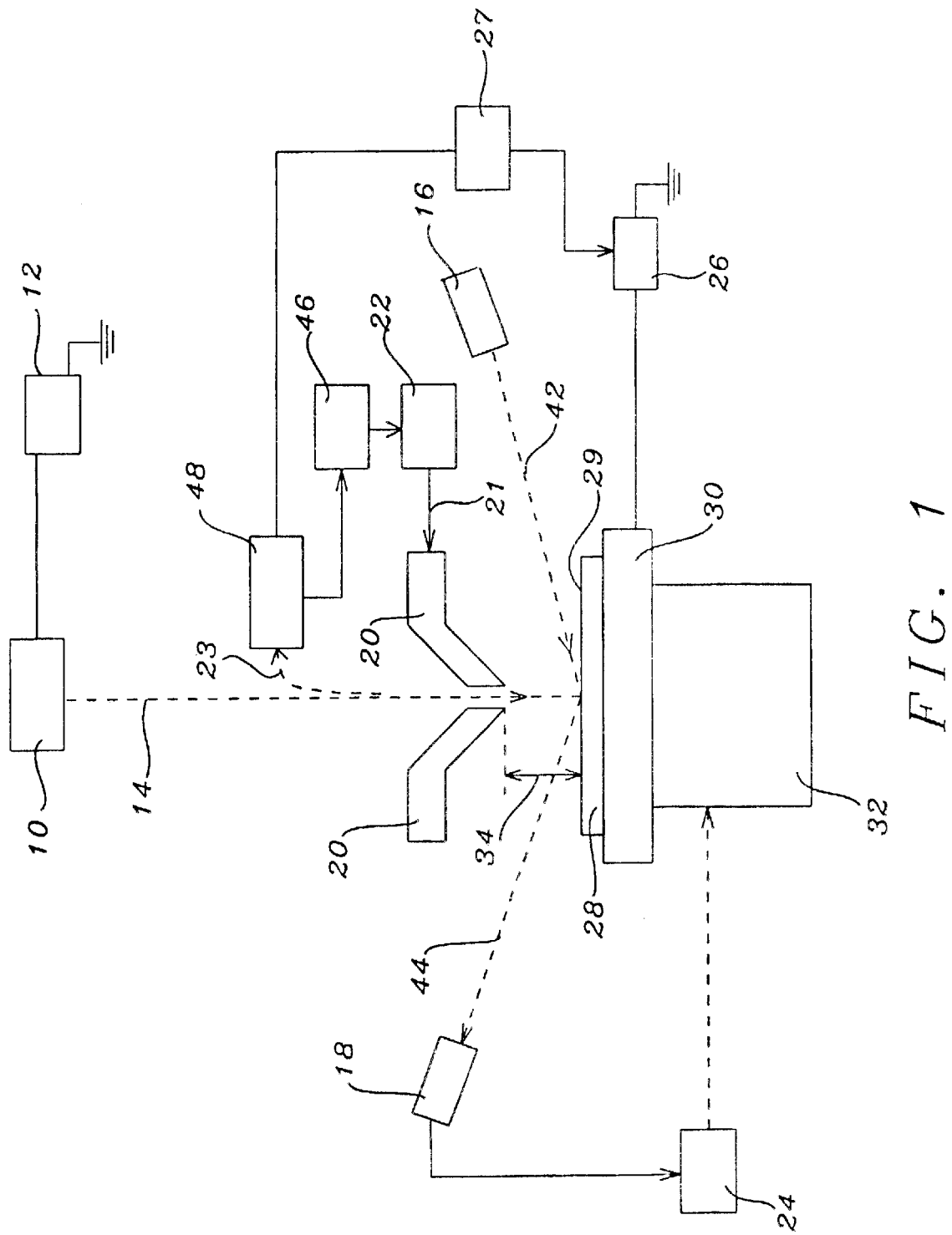
FIG. 1 shows a schematic diagram of a scanning electron microscope of this invention.
Figure 2:
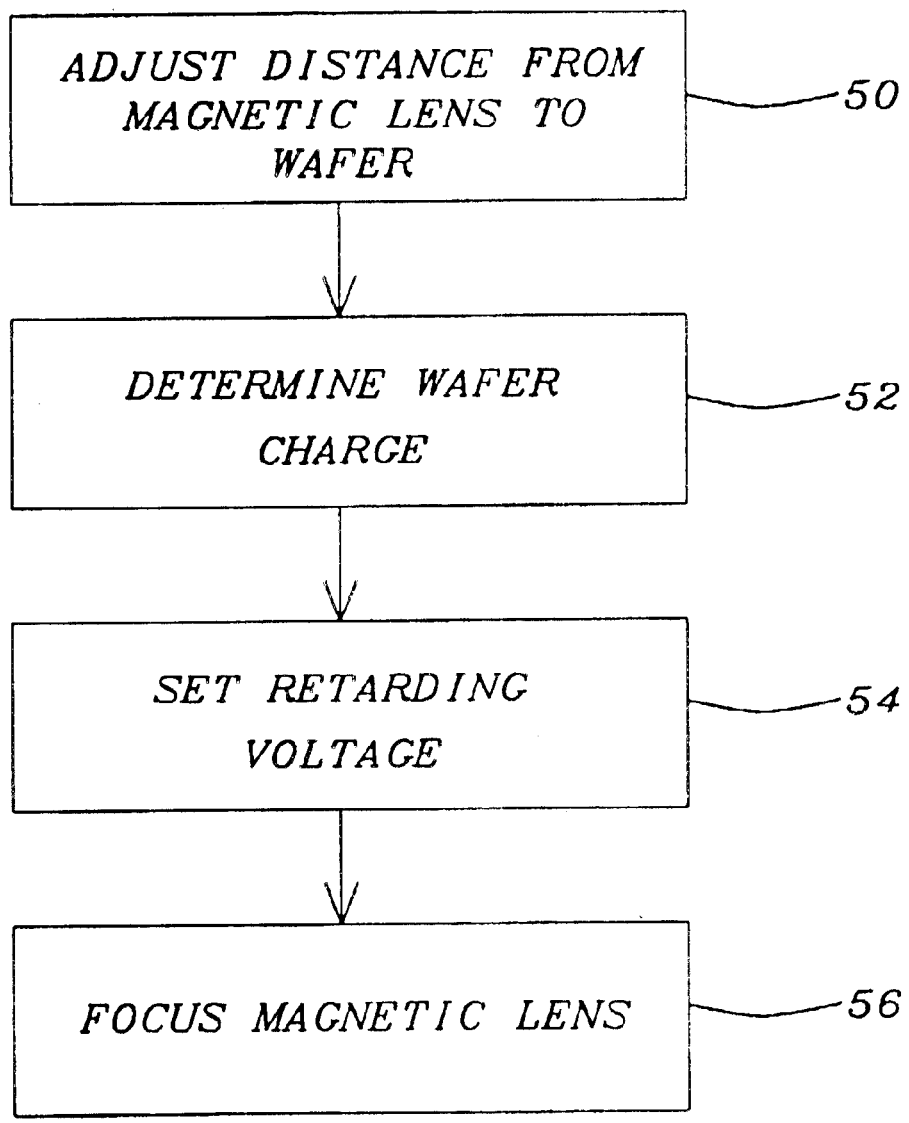
FIG. 2 shows a block diagram of the steps of the method of this invention.

Refer now to FIGS. 1 and 2 for a description of the preferred embodiments of the method and apparatus of this invention. FIG. 1 shows a schematic diagram of the apparatus of this invention. The apparatus shown in FIG. 1 is part of a scanning electron microscope, SEM, and has an electron beam source 10 which provides an electron beam 14 which is directed toward a specimen under test, in this example the top surface 29 of a wafer 28. A voltage supply 12 supplies an electron beam supply voltage, $V_O$, to the electron beam source 10. The electron beam supply voltage, $V_O$, is referenced to ground potential and supplies the accelerating potential to the electron beam. A magnetic objective lens 20 is used to focus the electron beam 14, which is focused using focusing current 21 supplied by a magnetic lens current control unit 22. An image detector 48 captures secondary electrons 23 from the wafer under observation and forms an image of the part of the wafer under observation. There is a focus feedback system 46 between the image detector 48 and the focus current supply, and a retarding voltage feedback system 27 between the image detector 48 and a retarding voltage control unit 26. The focus feedback system 46 and the retarding voltage feedback system 27 can be computers or other suitable feedback systems which can provide appropriate feedback and perform necessary calculations.

A wafer holder 30 is positioned by a means 32 to position the wafer holder 30, such as a piezoelectric actuator or the like. A retarding voltage control unit 26 supplies a retarding voltage, $V_R$, between the wafer holder 30 and ground potential. A wafer 28 to be measured is placed on the wafer holder 30. The accelerating voltage seen by the electron beam incident on the top surface 29 of the wafer 28 is equal to the retarding voltage subtracted from the electron beam supply voltage, $V_O - V_R$. There is means to determine the desired working distance 34 between the magnetic objective lens 20 and the top surface 29 of the wafer 28. In this example this means comprises a LASER 16 providing a LASER beam 42 which is reflected from the top surface 29 of the wafer 28. The reflected LASER beam 44 is detected by a LASER intensity control unit 18. The desired working distance 34 between the top surface 29 of the wafer 28 occurs when the light detected by the LASER intensity control unit 18 is a maximum. Any methodology which can control the working distance 34 can be used. A positioning feedback system 24 is provided between the LASER intensity control unit 18 and the means 32 to position the wafer holder 30. The positioning feedback system 24 controls the means 32 to position the wafer holder 30 to provide the desired working distance 34 between the magnetic objective lens 20 and the top surface 29 of the wafer 28. The positioning feedback system 24 can be a computer or other suitable feedback system which can provide appropriate feedback and perform necessary calculations.

As shown in FIG. 1, a wafer 28 is placed in the wafer holder 30. Information relating to the type of wafer, conductivity of the wafer, etc. is known. The first step of the method of this invention is to adjust the working distance 34 between the top surface 29 of the wafer 28 and the magnetic objective lens 20 to the desired working distance. This is accomplished by adjusting the working distance 34 between the magnetic objective lens 20 and the top surface 29 of the wafer 28 until the LASER intensity control unit 18 indicates a maximum. The position feedback system 24 allows this to be performed automatically and to be continually adjusted for different locations on the surface 29 of the wafer 28.

The wafer 28 will have accumulated a charge on the wafer due to previous processing and handling steps. This charge will give the wafer a voltage which will tend to repel the incident electron beam 14 from the surface 29 of the wafer 28 thereby distorting the image seen by the image detector 48. The retarding voltage, $V_R$, supplied by the retarding voltage control unit 26 counteracts the voltage due to the charge on the wafer 28. The next step is key to the method of this invention. In this step, after the desired distance between the wafer 28 surface 29 and the magnetic lens 20 has been achieved, is to adjust voltage supplied by the retarding voltage control unit 26 to achieve a good focus of the SEM image. The retarding voltage adjustment is achieved by the retarding voltage feedback system 27 between the image detector 48 and the retarding voltage control unit 26. The retarding voltage feedback system 27 adjusts the retarding voltage control unit 26 until good focus is achieved. The wafer charge can be determined from the amount of retarding voltage required to produce a good image focus.

The next step of the method of this invention is to adjust the current to the magnetic objective lens 20 to achieve the final focus. A focus feedback system 46 between the image detector 48 and the magnetic lens current control unit 22 provides control for the current 21 to the magnetic lens 20 provide the final image focus. The image detector 48, the focus feedback system 46, and the magnetic lens control unit 22 provide automatic final focus of the image.

Using the method of this invention in the sequence described the energy of the electron beam 14 impinging on the wafer surface 29 will always be the same and therefore the shrinkage effect of the electron beam 14 on a resist on the wafer surface 29 will always be the same. Using this method will avoid the problem of variable resist shrinkage.

FIG. 2 shows a flow diagram showing the method of this invention. As shown in the first box 50 of FIG. 2 the first step is to adjust the distance from the magnetic lens to the wafer 28. As shown in the next box 52 of the FIG. 2 flow diagram the wafer charge is determined by adjusting the retarding voltage. As shown in the next box 54 of the FIG. 2 flow diagram the retarding voltage is then set. As shown in the next box 56 the final step in the method is to focus the magnetic lens.

The wafer surface charge will vary with wafer pre-processing, and the charge distribution is not necessarily uniform. Using the method of this invention the energy of the electron beam incident on the wafer surface 29 will be the same and variability of resist shrinkage will be avoided.

While the invention has been particularly shown and described with reference to the preferred embodiments thereof, it will be understood by those skilled in the art that various changes in form and details may be made without departing from the spirit and scope of the invention.

What is claimed is:

1. A method of focusing a scanning electron microscope, comprising:
   providing a magnetic lens, an image detector, and a wafer holder;
   providing means for adjusting the position of said wafer holder;
   providing means for supplying a focus current to said magnetic lens;
   providing means for supplying a retarding voltage to said wafer holder;
   placing a wafer on said wafer holder;
   adjusting the position of said wafer holder, thereby adjusting the distance between the wafer placed on said wafer holder and said magnetic lens to a desired focus distance;
   adjusting the retarding voltage supplied to said wafer holder to achieve a best focus image of the wafer placed on said wafer holder at said image detector, after adjusting the distance between the wafer placed on said wafer holder and said magnetic lens to said desired focus distance; and
   adjusting said focus current to achieve a final focus image of the wafer placed on said wafer holder at said image detector, after adjusting the retarding voltage supplied to said wafer holder.

2. The method of claim 1 wherein said adjusting the distance between said wafer placed on said wafer holder and said magnetic lens to said desired focus distance comprises the use of a LASER and a LASER intensity control unit.

3. The method of claim 1 wherein said means for adjusting the position of said wafer holder comprises the use of a piezoelectric actuator.

4. The method of claim 1 wherein said means for adjusting the distance between said wafer placed on said wafer holder and said magnetic lens comprises a position feedback system.

5. The method of claim 4 wherein said position feedback system communicates with a LASER intensity control unit and said means for adjusting the position of said wafer holder.

6. The method of claim 4 wherein said position feedback system comprises a computer.

7. The method of claim 1 wherein said means for supplying a focus current to said magnetic lens comprises a magnetic lens current control unit and a focus feedback system.

8. The method of claim 7 wherein said focus feedback system communicates with said image detector and said magnetic lens.

9. The method of claim 7 wherein said focus feedback system comprises a computer.

10. The method of claim 1 wherein said means for supplying a retarding voltage to said wafer holder comprises a retarding voltage control unit and a retarding voltage feedback system.

11. The method of claim 10 wherein said retarding voltage feedback system communicates with said image detector and said retarding voltage control unit.

12. The method of claim 10 wherein said retarding voltage feedback system comprises a computer.

13. The method of claim 1 wherein the amount of said retarding voltage supplied to said wafer holder is determined automatically.

14. The method of claim 1 wherein the amount of said focus current supplied to said magnetic lens is determined automatically.

15. The method of claim 1 wherein the position of said wafer holder is determined automatically.

16. An apparatus for focusing a scanning electron microscope, comprising:
    a magnetic lens, an image detector, and a wafer holder;
    means for adjusting the distance between a wafer placed on said wafer holder and said magnetic lens to a desired focus distance;
    a retarding voltage supplied to said wafer holder, wherein said retarding voltage supplied to said wafer holder is adjusted to achieve a best focus image of the wafer placed on said wafer holder at said image detector, after adjusting the distance between the wafer placed on said wafer holder and said magnetic lens; and
    a focus current supplied to said magnetic lens, wherein said focus current is adjusted to achieve a final focus image, of the wafer placed on said wafer holder, at said image detector after adjusting the retarding voltage supplied to said wafer holder.

17. The apparatus of claim 16 wherein said means for adjusting the distance between the wafer placed on said wafer holder and said magnetic lens comprises a LASER and a LASER intensity control unit.

18. The apparatus of claim 16 wherein said means for adjusting the distance between the wafer placed on said wafer holder and said magnetic lens comprises a piezoelectric actuator connected to said wafer holder.

19. The apparatus of claim 16 wherein said means for adjusting the distance between the wafer placed on said wafer holder and said magnetic lens comprises a position feedback system.

20. The apparatus of claim 19 wherein said position feedback system communicates with a LASER intensity control unit and said means for adjusting the distance between the wafer placed on said wafer holder and said magnetic lens.

21. The apparatus of claim 19 wherein said position feedback system comprises a computer.

22. The apparatus of claim 16 wherein said focus current supplied to said magnetic lens is adjusted using a magnetic lens current control unit and a focus feedback system.

23. The apparatus of claim 22 wherein said focus feedback system communicates with said image detector and said magnetic lens.

24. The apparatus of claim 22 wherein said focus feedback system comprises a computer.

25. The apparatus of claim 16 wherein said retarding voltage supplied to said wafer holder is adjusted using a retarding voltage control unit and a retarding voltage feedback system.

26. The apparatus of claim 25 wherein said retarding voltage feedback system communicates with said image detector and said retarding voltage control unit.

27. The apparatus of claim 25 wherein said retarding voltage feedback system comprises a computer.

28. The apparatus of claim 16 wherein the amount of said retarding voltage supplied to said wafer holder is determined automatically.

29. The apparatus of claim 16 wherein the amount of said focus current supplied to said magnetic lens is determined automatically.

30. The apparatus of claim 16 wherein the distance between the wafer placed on said wafer holder and said magnetic lens is adjusted automatically.

* * * * *